Dec. 16, 1947. C. J. NIEDFELDT Plant Pat. 772

NEPHROLEPIS PLANT

Filed Dec. 6, 1946

WITNESS

Addison E. Avery

INVENTOR

CARL J. NIEDFELDT,

Rummler, Rummler & Davis,

ATTYS

Patented Dec. 16, 1947

Plant Pat. 772

UNITED STATES PATENT OFFICE

772

NEPHROLEPIS PLANT

Carl J. Niedfeldt, Wauwatosa, Wis.

Application December 6, 1946, Serial No. 714,479

1 Claim. (Cl. 47—59)

The present discovery relates to a new and distinct variety of Nephrolepis plant. The parent fern was a mutation from the well-known *Nephrolepis whitmanni,* which was a mutation from *Nephrolepis exaltata,* the common Boston fern.

About 1934 I discovered a small plant, which was believed to be a different form in structure, growing at the side of the pot of the parent plant. I transplanted this small fern and through a sexual reproduction since that time the characteristics of this new variety appear to be permanently fixed. At the present time there are ten plants of this new variety growing in my greenhouse. After several years of careful observation and experimentation, no spores have ever been found on the leaves or stems of the new variety. Through successive generations this fern has been produced by buds on runners both above and below the soil.

In the accompanying drawing,

Figure 1 is a photographic view of a potted plant typical of the new variety.

Fig. 2 is an enlarged view illustrative of the structure of a single pinnate leaf or frond, drawn schematically to show, within the area set off by a circle, a skeleton of the central rachis or main petiole stem and its primary and secondary branch petiole arrangement. In the upper right-hand quarter of the area of this circle the closely matted arrangement of the leaflets on these branches is shown. The tip of the frond at the upper left, outside of the circle, shows how the tiny leaflets thin out on the end of the spray.

This new variety of Nephrolepis is diminutive in size, the average plant being about 6 inches high and 12 inches wide. The individual fronds are of a different contour from the parent Boston fern and the leaflets are so minute that they are scarcely capable of being perceived by the eye as separate and distinct from the plant as a whole. In this new variety the main stalks undulate gracefully from the central clump and on an indivdual stalk, the minute leaflets and branches form an intertwining mass which gives the plant its delicate, feathery, bushy appearance. The leaves are generally pinnately compound and palmately decompound, with a harmonious curve to the individual leaflet.

Figure 1:
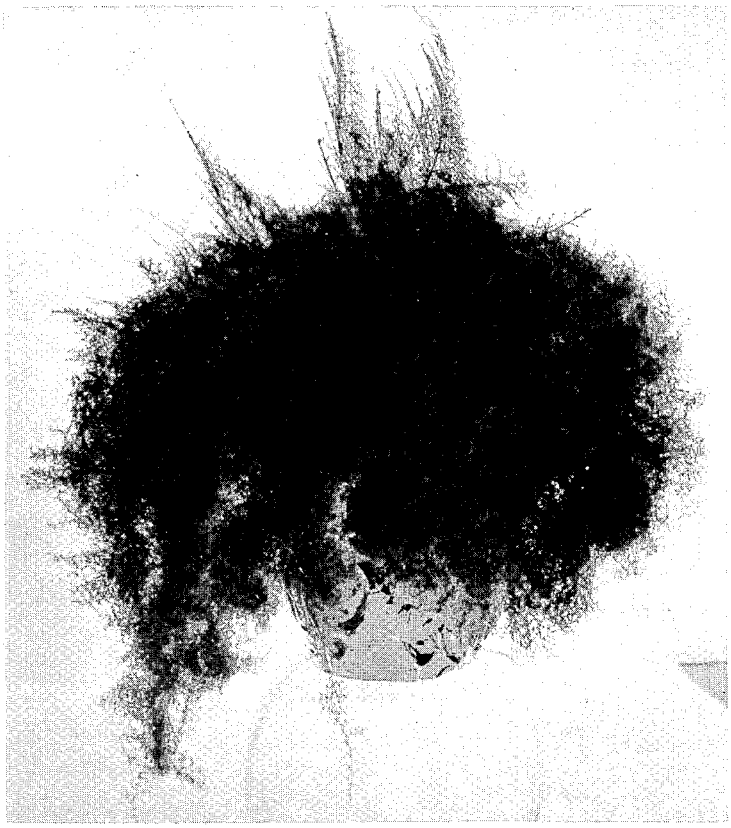
Figures 2, 3, 4:
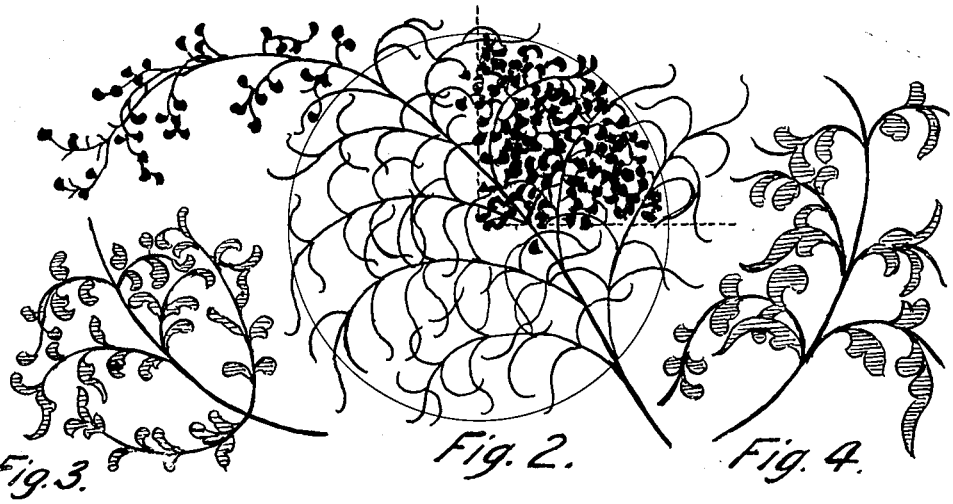
Fig. 3 is an enlarged fragmentary view of a frond showing the form and arrangement of leaves.
Fig. 4 is a view, greatly enlarged, showing the elongated formation of the older leaves.

The majority of the leaflets are of kidney shape, being wide at the tip and curvingly tapered toward the petiole, as shown in Figs. 2 and 3, but some of the older leaflets develop a second lanceolate lobe at their outer ends. The kidney-shaped leaflets average about 1 millimeter in width and 2 millimeters in length. The elongated leaflets average about 1 millimeter in width and 5 to 6 millimeters in length.

The color of the leaflets is green and may be identified according to "A Dictionary of Color by Maerz and Paul," by Plate 18–L–5.

The lacy effect of this new variety makes it most suitable for table decoration; whereas other varieties of this fern species, except when very young, are usually too bulky and large for table use.

Its dwarf size, feathery bushy appearance, and green coloring combine to make this fern a distinctive commercial product.

Having thus disclosed the invention, I claim:

A new and distinct variety of Nephrolepis plant, as herein shown and described, characterized particularly by its dwarf size, its feathery and lacy appearance; the dense, thick mass of its fronds; and the kidney shape of its leaflets.

CARL J. NIEDFELDT.

REFERENCES CITED

The following references are of record in the file of this patent:

"Garden Dictionary," published 1918 by Houghton, Mifflin Co., N. Y., page 526, article on Nephrolepis.